United States Patent
Muessig et al.

(10) Patent No.: US 9,821,154 B2
(45) Date of Patent: Nov. 21, 2017

(54) INTRAVASCULAR ELECTRODE LEAD AND INTRAVASCULAR STIMULATION DEVICE INCLUDING THE SAME

(71) Applicant: BIOTRONIK SE & Co. KG, Berlin (DE)

(72) Inventors: Dirk Muessig, West Linn, OR (US); Andrew B. Kibler, Lake Oswego, OR (US); Larry Stotts, Tigard, OR (US); Joseph Raven, Tigard, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 14/814,096

(22) Filed: Jul. 30, 2015

(65) Prior Publication Data
US 2016/0067474 A1    Mar. 10, 2016

Related U.S. Application Data

(60) Provisional application No. 62/045,582, filed on Sep. 4, 2014.

(51) Int. Cl.
*A61N 1/05* (2006.01)
*A61N 1/36* (2006.01)

(52) U.S. Cl.
CPC .......... *A61N 1/05* (2013.01); *A61N 1/36053* (2013.01); *A61N 1/056* (2013.01); *A61N 2001/36039* (2013.01)

(58) Field of Classification Search
None
See application file for complete search history.

(56) References Cited

U.S. PATENT DOCUMENTS

| | | |
|---|---|---|
| 5,733,925 A | 3/1998 | Kunz et al. |
| 7,239,924 B2 | 7/2007 | Kolberg |
| 2004/0098108 A1 | 5/2004 | Harder et al. |

(Continued)

FOREIGN PATENT DOCUMENTS

| | | |
|---|---|---|
| WO | 2014001191 | 1/2014 |
| WO | 2014001240 | 1/2014 |

(Continued)

OTHER PUBLICATIONS

European Search Report and Annex to the European Search Report on European Patent Application No. EP 15 17 8597, dated Jan. 14, 2016 (6 pages).

*Primary Examiner* — Ankit D Tejani
(74) *Attorney, Agent, or Firm* — Buchanan Ingersoll & Rooney PC

(57) ABSTRACT

An intravascular electrode lead and an intravascular stimulation device including the same. The intravascular electrode lead includes an electrode shaft; a plurality of filaments being made of a conductive, non-biodegradable material, running in longitudinal direction within the electrode shaft and protruding distally beyond a distal end of the electrode shaft, each filament terminating in at least one electrically active area; and a support member being arranged distally from the distal end of the electrode shaft and being dilatable from a compressed state to an radially expanded state, wherein the support member is attached to the filaments and made of a biodegradable material.

18 Claims, 5 Drawing Sheets

(56) References Cited

U.S. PATENT DOCUMENTS

| | | | |
|---|---|---|---|
| 2005/0085895 A1* | 4/2005 | Brown | A61F 2/0077 623/1.15 |
| 2006/0009830 A1 | 1/2006 | Atkinson et al. | |
| 2007/0191708 A1 | 8/2007 | Gerold et al. | |
| 2008/0033530 A1 | 2/2008 | Zberg et al. | |
| 2008/0033533 A1 | 2/2008 | Borck et al. | |
| 2008/0033576 A1 | 2/2008 | Gerold et al. | |
| 2012/0035691 A1 | 2/2012 | Tockman et al. | |
| 2012/0116499 A1 | 5/2012 | Goetzen et al. | |
| 2013/0206454 A1 | 8/2013 | Cattaneo et al. | |
| 2014/0180196 A1* | 6/2014 | Stone | A61B 18/1492 604/21 |

FOREIGN PATENT DOCUMENTS

| | | |
|---|---|---|
| WO | 2014001241 | 1/2014 |
| WO | 2014001321 | 1/2014 |

\* cited by examiner

INTRAVASCULAR ELECTRODE LEAD AND INTRAVASCULAR STIMULATION DEVICE INCLUDING THE SAME

CROSS-REFERENCE TO RELATED APPLICATIONS

This patent application claims the benefit of co-pending U.S. Provisional Patent Application No. 62/045,582, filed on Sep. 4, 2014, which is hereby incorporated by reference in its entirety.

TECHNICAL FIELD

The present invention refers to an intravascular electrode lead and an intravascular stimulation device including the same.

BACKGROUND

Neurostimulation is the therapeutic alteration of activity in the central, peripheral or autonomic nervous systems by means of implanted devices. Neurostimulation may treat a variety of symptoms or conditions, for example, vagus nerve stimulation (VNS) is an adjunctive treatment for certain types of intractable epilepsy and treatment-resistant depression. A neurostimulator (or implantable pulse generator (IPG)) is a battery powered device designed to deliver electrical stimulation to the brain, central and peripheral nervous system.

The vascular system contains numerous locations within it and in contact with it which are electro-active and present the possibility of therapeutic electrical stimulation. One example of such a location is in the right brachiocephalic vein-SVC junction by which runs the right vagus nerve. Stimulation of the vagus nerve has been shown to result in an anti-inflammatory effect and a reduction in sympathetic drive which is beneficial to patients suffering from a variety of conditions including, for example, heart failure, acute ischemic attack, and atrial and ventricular arrhythmias.

Other locations are in the arterial system. One example of such a location is the carotid artery, especially the region in or around the carotid sinus, common carotid artery, the internal carotid artery and/or the external carotid artery. Also possible are other locations like the renal artery for stimulation of renal nerves, for example.

Trans-vascular stimulating electrodes exist for chronic application, for example, for phrenic nerve stimulation; however, most of them are designed for small vessels and cannot be used in large veins. Hence, a system capable of delivering or recording electric fields in a vessel near a neuroactive target location being compatible with large veins would be advantageous.

Trans-vascular stimulation of the vagus nerve has been demonstrated previously with basket catheters. One problem with common expandable basket-style stimulation catheters is that they are designed for acute stimulation and are not appropriate for chronic stimulation.

In common intravascular neurostimulation devices, electrodes are positioned within a blood vessel (for example, a jugular vein, superior vena cava, or inferior vena cava) and are used to trans-vascularly stimulate nervous system targets located outside or within the walls of the vasculature. For maintaining the electrodes in contact with the blood vessel wall anchors have been developed. Such anchors include structural features that allow the anchor to radially engage a vessel wall. The anchor may include a band, sleeve, mesh or other framework formed of shape memory materials (for example, Nitinol or shape memory polymer) or other non-biodegradable materials like, for example, stainless steel. However, safe explant of the electrodes at a later date, even after many years of biological interaction, may be desired, which cannot be achieved in presence of permanent anchors since they will be encapsulated fast by the biological system. In addition, continuous mechanical interface against the vessel wall with pressure from the anchor or stiff materials used in an anchor is not desirable because of its potential to cause vessel irritation and enlarged capsule formation.

Trans-vascular stimulation is also performed in cardiology, where the same drawbacks apply. For multi-chamber pacing of the heart it is commonly known to implant cardiac stimulation electrode leads within the coronary vein system, in particular within the Coronary Sinus vein ("CS"), in order to stimulate cardiac tissue, especially the left atrium and/or chamber. For anchoring of these electrode leads several anchoring mechanisms are known, which are mostly not explantable. For example, special formed parts of the lead such as helically shaped bodies are known to those familiar with the art. In this embodiment, stimulation pulses are provided by cardiac pacemakers, cardioverter or implantable defibrillators, which are also summarized with the term "implantable pulse generator".

The present invention is directed toward overcoming one or more of the above-mentioned problems.

SUMMARY

One or more of the drawbacks of the state of art may be avoided or at least reduced by use of the inventive intravascular electrode lead for an intravascular stimulation device, as defined in claim 1. The intravascular electrode lead comprises an electrode shaft; a plurality of filaments being made of a conductive, non-biodegradable material, running in longitudinal direction within the electrode shaft and protruding distally beyond a distal end of the electrode shaft, each filament comprising at least one electrically active area; and at least one support member being arranged distally from the distal end of the electrode shaft and being dilatable from a compressed state to an radially expanded state, wherein the support member is attached to the filaments and made of a biodegradable material. The electrically active area is defined as an area on or at each filament, at which galvanic or capacitive coupling exists to the surrounding tissue. In other words, at the electrically active area, a therapeutical and/or sensorial interface to or a place of interaction with the surrounding tissue takes place. In this context, explicitly referred to is an interface to record physiological signals and/or to a place of interaction to stimulate the surrounding tissue. Preferably, the electrically active area is at the distal portion of each filament, preferably at the distal end portion of each filament, and more preferably at the distal end of each filament.

The present invention especially provides a system capable of delivering or recording electric fields in a vessel near a neuroactive target location, wherein this system is compatible with large veins and also may be safely explanted at a later date, even after many years of biological interaction. The inventive system includes means for a new kind of multi-stage fixation of the explantable electro-active medical device. The intravascular electrode lead is used for intra- or trans-vascular stimulation or recording, and particularly useful to an embodiment which allows stimulation of the vagus nerve trans-vascularly via the superior vena cava ("SVC"). In another embodiment, it is also useful to stimulate cardiac tissue via one of the coronary veins, in particular the coronary sinus vein ("CS"). This is achieved by use of a multi-stage fixation mechanism, wherein a first stage of fixation is achieved via mechanical fixation of an at least one bio-degradable support member to the target vascular location. The at least one support member temporarily supports a non-absorbable filament which provides the means of electrical interaction with the tissue. During its biological encapsulation the at least one support member dissolves over a certain time and thereby releases the non-absorbable filaments, which are at this second stage under normal conditions biologically encapsulated and therefore fixated to the surrounding tissue (especially vascular tissue) (second stage of fixation). The filaments are especially designed to be oriented relative to each other and to an intravenous tether so as to allow extraction from their encapsulation by way of tethered pulling. The end result, regardless of whether the electrode device is explanted, is a highly compliant trans-vascular stimulation device, which minimizes stenosis and provides means for selective stimulation and/or sensing along the vessel walls.

Thus, the problem of vascular fixation of the electrodes with the possibility of later explant is solved via a multi-stage fixation approach with a biodegradable first mechanical fixation stage and a tether capable of extracting a thin filament-based second, long-term biological second fixation stage. The first fixation stage is accomplished via rapid mechanical fixation of the biodegradable material to the vessel wall. This could be accomplished, for example, via expansion of a mesh-like support member such that its outward pressure against the vessel wall holds it in place. This first stage of fixation is designed to last long enough to allow biological encapsulation-based fixation (stage 2) of the long-term thin filaments before the support member dissolves.

It is important to note that the multi-stage fixation mechanism taught in this disclosure retains benefits beyond allowing later explant. Multi-stage fixation of intravascular electrodes permits design of highly flexible electrode structures which reduce the propensity of stenotic capsule formation along the vessel walls. In doing so, the long-term biocompatibility of a multi-stage fixation solution is greatly improved over existing semi-rigid techniques. Such a multi-stage fixation solution is applicable to future generation miniature leadless intravascular stimulation or monitoring devices which may target the vagus, and/or localized baroreceptors for therapy.

The thin filaments may be tethered directly or via an intravascular tether which connects to an electro-active component capable of electrically interfacing with the thin filaments for stimulation or recording. This tether may be used to pull the thin filaments out from its biological fixation tunnel if and when explant is desired.

Hence, the intravascular electrode lead is preferably adapted to allow retraction of the filaments into the electrode shaft prior to extraction of the electrode lead. Therefore, the electrode shaft may be composed of a single or multi-lumens. Various lumens may be used to house permanent lead components like the filaments or temporary components used during implant or explant for the delivery of flushes or to provide mechanical reinforcement during deployment and retraction procedures.

The long-term electro-active filaments may be coated with a biocompatible electrically insulating coating along part of their length and/or a portion of their circumference in order to directionally steer a stimulating electrical field toward a therapeutically desirable location, such as the vessel wall.

The long-term electro-active filaments may be electrically isolated from each other, and the tether to which they are connected may contain individual connecting leads for each filament, such that a control device to which the connecting leads are connected may select one or a combination of filaments with which to stimulate or sense. Each filament may have one or more regions for electrical sensing and/or current delivery intended to generate one or more electric fields. Thus, the filaments are preferably connected to an electrically conducting tether running within the electrode shaft. The tether may comprise connecting leads for each of the filaments.

Each filament may contain a plurality of individually conductive elements, for example, wires, which each terminate in an active area in galvanic communication with surrounding tissue at different locations along the filament's length. Each conductive element may be individually addressable so that selection of, and stimulation from, each channel's active area excites a distinct region of tissue. In this way, longitudinal selectivity may be achieved with the device. Furthermore, each filament may be individually addressable so as to allow circumferential selectivity of stimulation delivery, in order to target the region of the vascular which best elicits the desired effect of stimulation. The selection of stimulating filament and electrode along the selected filament(s) is provided for by means of a plurality of contacts at the proximal end of the tether, where, for small numbers of addressable stimulating electrodes, each contact is electrically and individually connected to a stimulating electrode site at the distal end of a conductive filament, located at the distal end of the tether. For implants with large numbers of stimulating electrodes, electrode selection is provided for by means of a multiplexer micro-circuit embedded at the branching point of the distal end of the tether.

The conductive filament branching point at the distal end of the tether may be located radially along the perimeter of the support member, so as to allow for the exit of filaments along the vascular wall such that the filaments remain in contact with the vascular wall along their entire length. In this way, the resistance to blood flow and possibility of thrombogenesis is greatly reduced. Upon explant, the tether is able to pull the electro-active long-term filaments from their encapsulation via application of uni-directional force in an axial direction with the tether.

The non-absorbable filaments may be further configured to follow a sloping serpentine pattern, such that the natural pulsatile stretching of vessel walls is allowed for in the longitudinal direction. This feature prevents continuous translation of the filaments along the encapsulation tunnel inside the vessel after the dissolvable fixation method has dissolved, greatly reducing formation of an enlarged stenotic capsule.

Various surface morphologies along the tether, the support member or the filaments may be used to target specific types of tissue ingrowth and encapsulation within the vessel. Examples of surface morphologies intended to optimize the device-tissue interface may be: (a) electro-polished surfaces, (b) open cell foams, (c) closed cell foams, (d) dipped coatings of parylene or silicone, and (e) sprayed coatings of parylene or silicone.

Preferably, the support member is made of a biodegradable metal or metal alloy. Biodegradable materials have been developed, inter alia, on the basis of polymers of synthetic nature or natural origin. Because of the material properties, but particularly also because of the degradation products of the synthetic polymers, the use of biodegradable polymers is still limited. Furthermore, the support member needs to withstand high mechanical strains and must meet specific requirements for modulus of elasticity, brittleness, and moldability, depending on its design and functionality.

Most preferred the biodegradable metal alloy includes magnesium, iron and/or zinc as a main alloy component or an alloy component. The main component is the alloy component whose amount by weight in the alloy is the greatest. The main component preferably amounts to more than 90% by weight, more 50% by weight, and in particular more than 70% by weight. The preferred main alloy is magnesium. Suitable alloys are Magnesium-Zinc-Calcium alloys, which are subject matter of the Assignee's International Publication Nos. WO 2014/001321 and WO 2014/001241, Magnesium-Aluminum alloys as disclosed in Assignee's International Publication No. WO 2014/001240, or Magnesium-Aluminum-Zinc alloys as disclosed in Assignee's International Publication No. WO 2014/001191. All of these documents are incorporated herein by reference in their entireties.

The term biodegradable (or biocorrodible or bioabsorbable or bioresorbable or biodissolvable) as used herewith is understood as the sum of microbial procedures or processes caused by the presence of bodily media, which result in a gradual degradation of the structure comprising the material. At a specific time, the total support member, or at least the parts of the support member which comprises the biodegradable material, loses its mechanical integrity. The specific time depends on the material composition of the alloy used for the at least one support member. In an embodiment, the intravascular electrode lead comprises more than one support member, wherein each of the more than one support members may have various alloys with different material compositions, so that the specific time up to the loss of mechanical integrity of each of these support members can vary. The degradation products are mainly resorbed by the body, although small residues being in general tolerable.

The at least one support member may further include a radially expandable framework of struts. For example, the at least one support member may have a stent-like or graft stent-like design. In the following text, all of the examples explained or mentioned up to here ("framework of struts", "stent", "stent-like or graft stent-like design") may also be referred to as "stent" or "stent-like". Hence, according to an embodiment of the disclosed invention, a biodegradable stent is constructed as the at least one support member with inter-woven or mechanically affixed conductive, non-biodegradable filaments. The filaments may be connected to an electrically conducting, biologically compatible tether. The tether comprises conductors, which facilitate electrical communication from an IPG to the proximal end of the at least one filament, and comprises elements of sufficient tensile strength, which facilitate extraction of the at least one filament, after the at least one support member has dissolved. The conductors and/or the elements of sufficient tensile strength are known from commonly known implantable leads like, for example, cardiac electrode leads. The tether is preferably similar in construction to the body of a commonly known pacemaker lead, containing a plurality of insulated conductors and an outer insulating jacket. Those skilled in the art are familiar with a variety of pacemaker lead configurations, from helical-wound conductor construction, concentric helical conductor construction, and multi-lumen lead body construction.

The present invention is compatible with attachment to lead body constructions known to those skilled in the art and in such an arrangement, the lead body is referred to as the tether. A steerable delivery tool capable of expanding the stent and allowing blood flow through its expansion mechanism allows test positioning of the stent/filaments by test stimulation or recording of the conductive filaments via the tether prior to full expansion of the device onto the vessel walls. The thickness and composite or alloy composition of the biodegradable stent is designed to last sufficiently long to allow biological encapsulation and fixation of the long-term electro-active filaments of the electrode lead. The filaments may comprise tissue fixtures. For example, the filaments may have small anchors along their length and/or at their distal end in order to prevent the pulsatile flow of blood from working the filaments from their encapsulation once the biodegradable stent has been dissolved. Examples of potential anchor shapes are spheres, barbs, fillets, or bumps. Further examples are disclosed, for example, in Assignee's U.S. Pat. No. 7,239,924.

The at least one support member may further preferably include electrode contact elements, which either build the electrically active area of the filaments or which are fixedly and electrically attached to the electrically active of the filaments. The electrode contact elements may be distributed circumferentially and longitudinally over the at least one support member. The electrode contact elements may include an electrode contact zone, which is displaced radially outwardly in the expanded state of the support member. The electrode contact elements may include an electrode head electrically connected with one of the filaments and providing a therapeutic contact surface. The therapeutic contact surface is a surface in galvanic communication with surrounding tissue with the purpose of producing an excitatory electrical field in the surrounding tissue. The therapeutic contact surface may perform a sensing function whereby its galvanic interface is used to record electrical potentials in the surrounding tissue.

According to another embodiment, the filaments are replaced in total or parts by a flexible printed circuit. An electrode head is being assembled on the printed circuit. The printed circuit is being composed of, for example, liquid crystal polymer with embedded conductive filaments. The circuit is adapted so as to conform to the at least one support member and allow encapsulation of itself into the vessel wall as the at least one support member dissolves. Electrical components may be embedded into the non-absorbable circuit to provide additional functionality such as multiplexing, power generation, stimulus generation, or sensory functions. This circuit is part of the tether. For example, in an embodiment of the present invention, the electrode lead comprises three input conductors, sixteen (16) output conductors and a de-multiplexing circuit. The input conductors are part of the tether and are commonly known, for example, from pacemaker leads. The de-multiplexing circuit and the output conductors are integrated within the printed circuit. This arrangement is preferable, so that the flexibility of the tether is maintained by not requiring it to contain 16 conductors. In a preferable embodiment, the tether contains three input conductors, which are all connected to an input stage of the de-multiplexing circuit, the three input conductors include: a first input conductor, which provides power and digital communication; a second input conductor, which provides analog stimulation drive; and a third input conductor, which provides a voltage reference. The 16 output conductors for stimulating the tissue are connected to the output stage of the de-multiplexing circuit, located at the distal end of the tether, and the proximal end of the filaments. This de-multiplexing circuit is configured to provide a means of filament selection controlled by the digital communication conductor such that only the selected filament(s) are driven from the analog stimulation drive conductor of the tether.

Portions of the at least one support member should be sufficiently x-ray opaque to allow for determination of orientation during implant. This allows for rotational control of implant placement relative to biological structures. At least one portion of the non-biodegradable tether contains a portion sufficiently opaque to X-rays and configured to allow means of identification of manufacturer and model via fluoroscopy. In addition, also the filaments may include x-ray opaque sections. In summary, at least one of the at least one support members, the tether, or the filaments may include radiopaque markers.

Various drug eluting components may be manufactured with the tether, filaments, or the at least one support member intended: (a) to modulate the biofouling response, (b) modulate inflammation, (c) optimize tissue ingrowth, or (e) optimize lead extraction. Pharmaceuticals which may be utilized with the aforementioned device components include, for example, corticosteroids, Cox-2 inhibitors, platelet activating factor (PAF) inhibitors, thrombolytics, and anticoagulants. Hence, at least one of the support member, the tether or the filaments preferably includes drug eluting components.

According to another aspect of the present invention, there is provided an intravascular stimulation device comprising a pulse generator; and the above mentioned intravascular electrode lead.

Further embodiments, features, aspects, objects, advantages, and possible applications of the present invention could be learned from the following description, in combination with the Figures, and the appended claims.

DESCRIPTION OF THE DRAWINGS

These and other aspects and advantages of the present invention will become apparent and more readily appreciated from the following descriptions taken in conjunction with the drawings in which.

DETAILED DESCRIPTION

Figure 1:
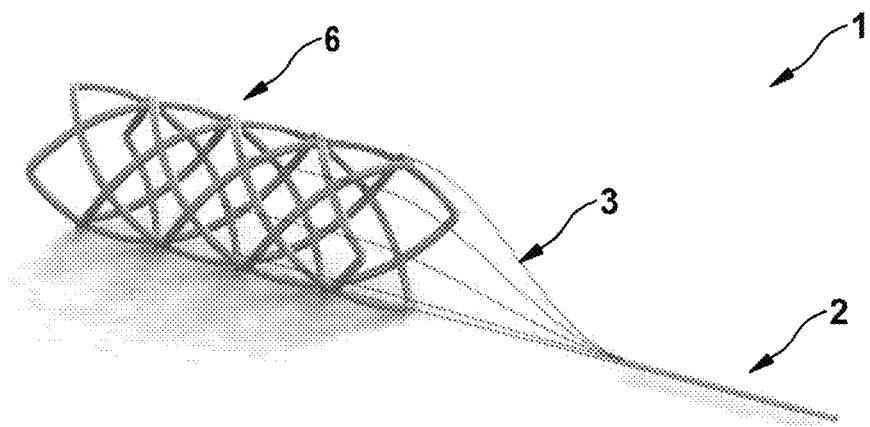
FIG. 1 shows an example of the inventive electrode lead for trans-vascular stimulation of nerve tissue.

Reference will be made in detail to embodiments of the present invention. The embodiments described herein are exemplary, explanatory, illustrative, and used to generally understand the present disclosure. The same or similar elements and the elements having same or similar functions are denoted by like reference numerals throughout the descriptions.

General Concept

FIG. 1 shows an example of the inventive electrode lead 1 for intravascular stimulation of nerve tissue. As can be seen, the electrode lead 1 has an elongate electrode shaft 2 formed as an elongate tube with at least one filament 3, which runs fixedly attached in longitudinal direction within the electrode shaft 2. The shaft 2 has the shape and material of a commonly known implantable electrode lead. A support member 6, that could be dilated from a compressed to a radially expanded state, is arranged distally from the distal end of the elongate shaft 2 and is temporarily attached to the electrode shaft by the at least one filament 3, which protrudes distally beyond the distal end of the electrode shaft 2. The proximal end of this electrode lead 1 can be electrically coupled to a medical implant like, for example, an implantable pacemaker, an implantable defibrillator or an implantable nerve stimulator (intravascular neurostimulation device). Therefore, the proximal end is carried out like a commonly known implantable electrode lead with a plug coupled to the shaft and electrical contacts, which are electrically connected to the filaments 3.

The support member 6 is made of a stable, radially strength material, which degrades, resorbs, dissolves, or corrodes in vivo over time (i.e., is biodegradable) with the result, that the filaments 3 are released from the support member 6. The time to a loss of integrity of the support member 6 should be set to up to 2 months, preferred up to 1 month, more preferred to three weeks, and most preferred to one to two weeks after implanting into a body vessel. Suitable materials are, for example, biodegradable (i.e., biodissolvable, bioresorbable, biocorrodible or bioabsorbable) metal alloys with a main component selected from magnesium, iron or zinc, preferably from Magnesium-Zinc-Calcium alloys, Magnesium-Aluminum alloys or Magnesium-Aluminum-Zinc alloys.

The attachment of the filaments 3 to the support member 6 is arranged by at least one electrode contact element, which either builds the electrically active area at the distal part of the filaments 3, or which is fixedly attached to the distal end of the filaments 3.

Further features of the electrode lead can be:

Radiopacity of the at least one support member 6.

Coating on the outside and/or the inside of the at least one support member 6 for releasing of therapeutically active substances like drugs.

In a further embodiment, an electrode lead with two or more support members is provided, each of these support members having at least one releasable filament attached. In one variant, the at least one filament is connected to all of these two or more support members, so that a simultaneous stimulation at all support members is possible. In another variant, different sets of at least one filament are attached to each of these two or more support members. With this configuration, a sequential stimulation with different stimulation regimes can be performed. Both variants can be used alternatively or cumulatively.

In one configuration of two or more support members, these two or more support members are placed in series along the longitudinal axis of the electrode lead, for example, one support member in distal elongation before the other support member. Preferably, the distance between the support members is adjustable. In another configuration, the electrode lead is configured in the manner that the two or more support members are placed in a substantially parallel manner at different arms of the electrode lead, wherein each arm has a fixed or adjustable length.

With this configuration, it is possible to place each of these two or more support members in different vessel branches. For example, an electrode lead with a first and a second support member is configured to be placed with the first support member in the internal carotid artery and with the second support member in the external carotid artery, so that a baroflex receptor is "sandwiched" between the first and second support member. Each of these support members comprise at least one filament as mentioned before, each of these support members can be driven simultaneously and/or sequentially.

Alternatively, this configuration can also be performed by using a bifurcated support member, which has at least two separate branches, each of these branches are configured to be placed in different vessels. Each branch has different sets of at least one filament. An example for a bifurcated support member can be a so called bifurcated stent, which is made of the materials disclosed in this application.

Designs

Figure 2:
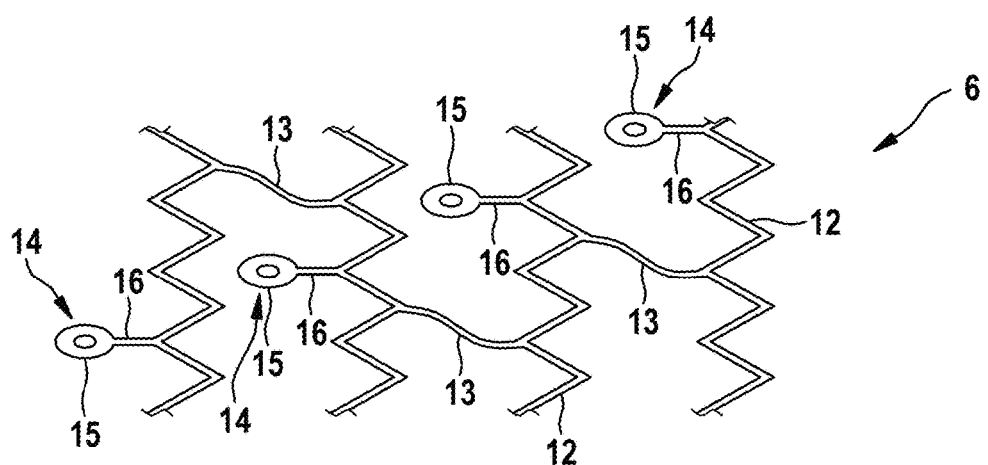
FIG. 2 shows a slotted tube stent as support member of an intravascular electrode lead.

The at least one support member 6 can be of the design and shape of an implantable stent. An example for a design of a mesh like support member 6 is shown in FIG. 2. In this example, the at least one support member 6 is formed in the manner of a slotted tube stent, which forms a type of framework structure from main meander struts 12 and longitudinal bridges 13. Electrode contact elements 14 are distributed circumferentially and longitudinally over the at least one support member 6 at various meander points of the main meander struts 12. The electrode contact elements 14 are each formed in this case by an electrode contact zone 15, freed from surrounding material of the support member 6 by corresponding cutouts, at a connecting web 16 carrying said elements for mechanical connection thereof to the at least one support member 6.

Figure 3:
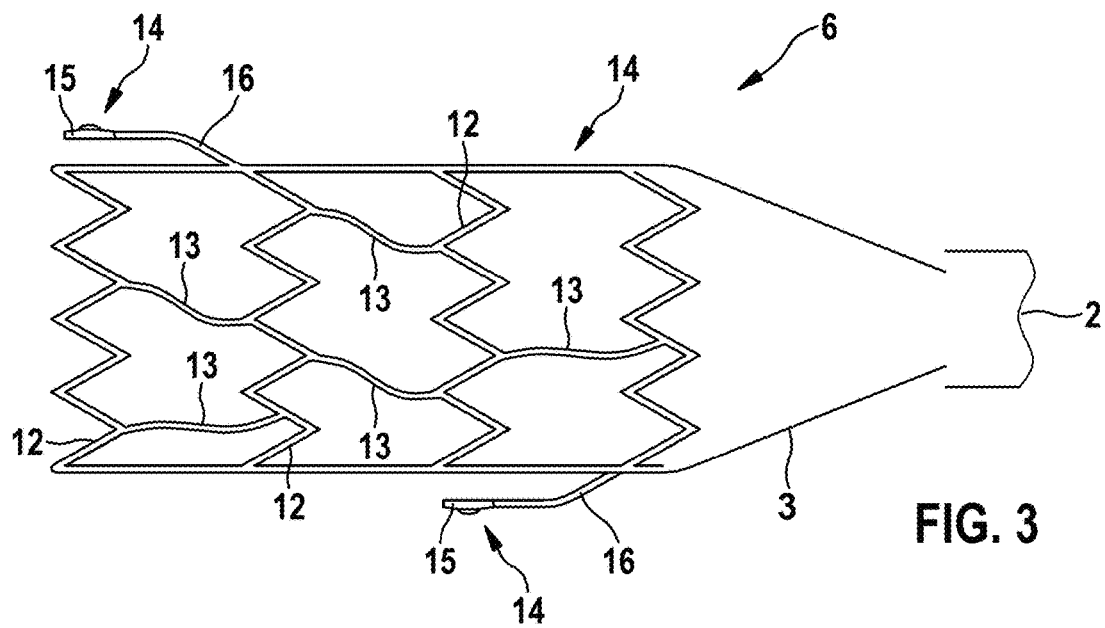
FIG. 3 shows details of contact zones of the support member of FIG. 2.

As can be seen in FIG. 3, the contact zones 15 of the electrode contact elements 14 are displaced radially outwardly as a result of the expansion of the at least one support member 6, such that a reliable contact between the contact zones 15 and the bodily tissue, for example, of the SVC or the carotid arteries is ensured. In this state, the contact zones 15 can then be supplied by an intravascular stimulation device like a pulse generator with a low voltage stimulation pulse. In another application of the electrode lead, it is implanted within the renal artery. At this location the contact zones 15 of the support member 6 can be supplied by an HF source with corresponding HF energy, and corresponding nerve modulation can be carried out at the contact zones for therapeutic purposes. In the latter application, the electrode lead may have an interface in a proximal portion of the electrode shaft 2 (FIG. 1) for extracorporeal coupling with an extracorporeal HF source.

Figure 4:
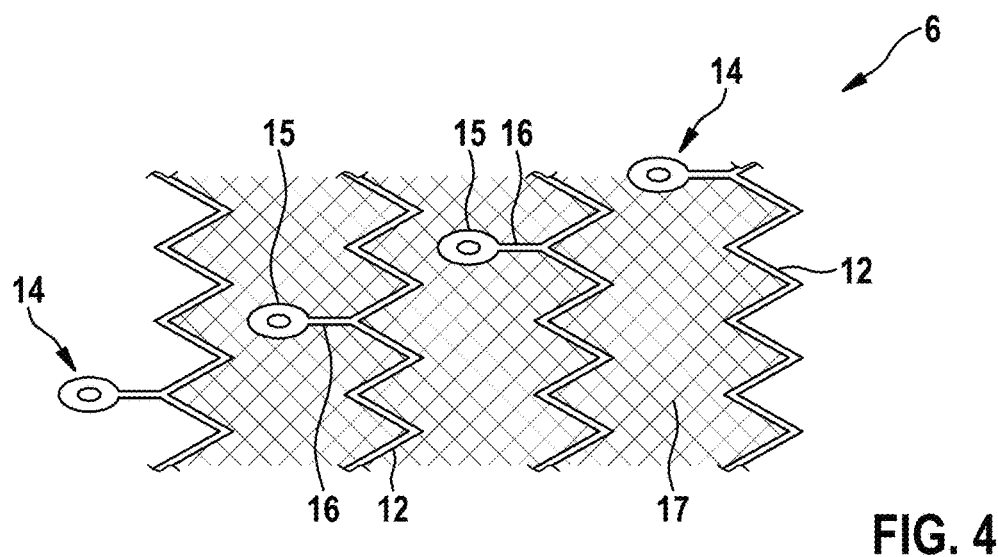
FIG. 4 shows a stent graft as support member of another intravascular electrode lead.

FIG. 4 shows a section of an alternative embodiment the at least one support member 6, which is designed in the manner of a stent graft. The at least one support member 6 again has main meander struts 12, which are interconnected in the longitudinal direction by a flexible woven fabric 17 however. Similarly to the above mentioned embodiment, electrode contact elements 14 sit on the main meander struts 12.

Figure 5:
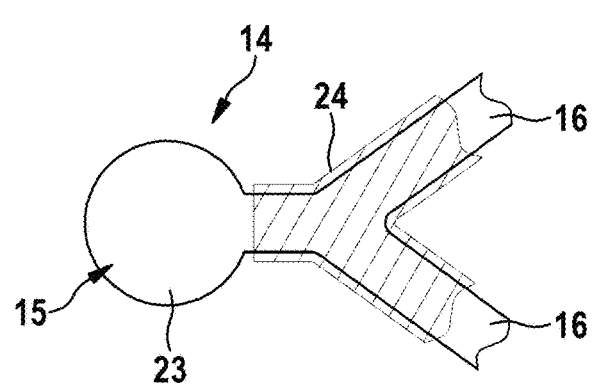
FIG. 5 shows a paddle formed as electrode contact.

There are different embodiments of the electrode contact elements and contact zones:

FIG. 5 shows electrode contact elements 14, of which the contact zone 15 is formed as a closed therapeutic contact surface 23 having a flat, paddle-like form. This is decoupled galvanically from the connecting webs 16, and thus from the rest of the at least one support member 6, in a suitable manner, for example, by a thin plastics coating 24 and/or a plastic element, which connects the paddle formed contact surface 23 and the connecting web 16. The paddle in this case is formed by the electrically active area of a filament 3, wherein in this embodiment the electrically active area is at its distal end.

Figure 6:
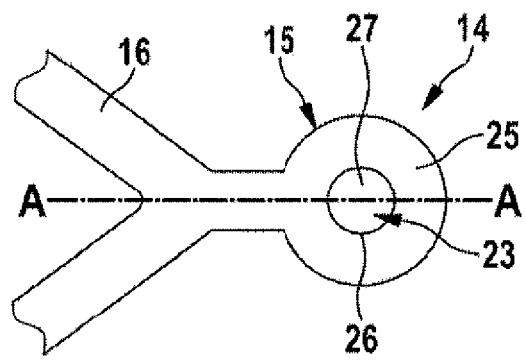
FIGS. 6-7 show an electrode contact element having an electrode contact zone.
Figure 7:
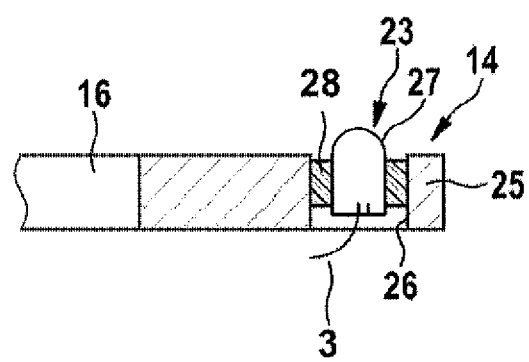

The variant illustrated in FIGS. 6 and 7 shows an electrode contact element 14 having an electrode contact zone 15, which forms an annular mechanical holder 25 in the form of an aperture 26. An electrode head 27 is housed in this aperture 26 as a therapeutic contact surface 23, which is insulated galvanically in the aperture 26 via a suitable ring insulator 28. The electrode head 27 itself is supplied with therapeutic stimuli via the electrically active area of the filaments 3, as also shown in FIG. 7. In this embodiment, and also in the other embodiments, the filaments 3 may be furnished with at least one break or weak point, which is preferably at or near the electrically active area or the electrode head 27. This at least one break or weak point enables an easy explantation of the filaments.

The filaments preferably extend on the outer surface of the at least one support member, which is the surface faced to the surrounding tissue. This ensures that the filaments are stowed and fixed between the at least support member and the surrounding tissue. If, as shown in FIG. 7, the filaments are attached to an electrode head, the filament, at its more proximal portion, may be looped through one of the recesses between the main meander struts 12 and the longitudinal bridges 13, respectively, the gaps in the flexible woven fabric 17. In another variation, the filament is insulatively looped through the aperture 26 within the ring insulator 28.

Figure 8:
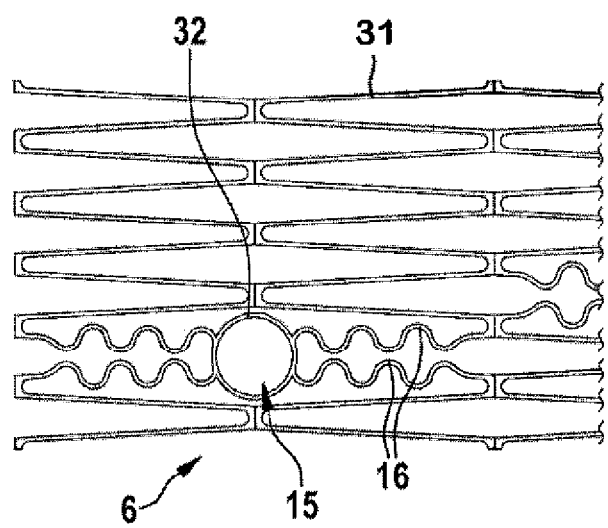
FIGS. 8, 9 and 10 show a support member based on a slotted tube design.
Figure 9:
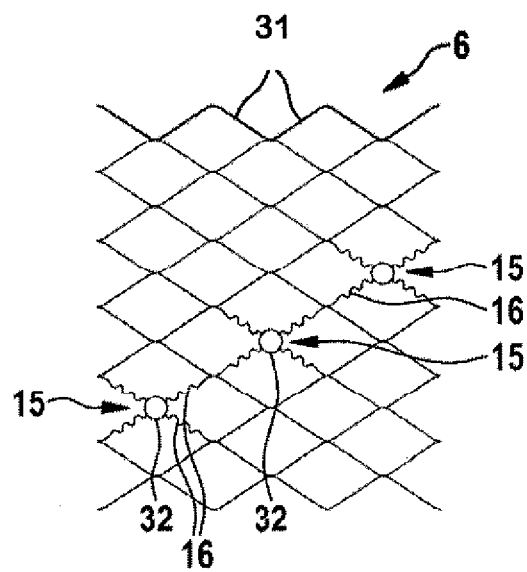
Figure 10:
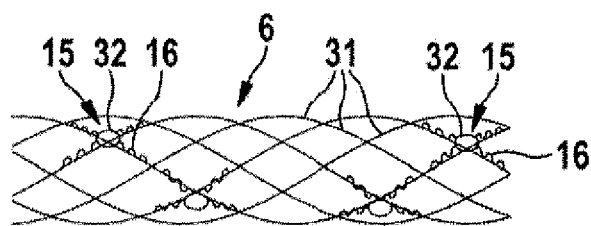

FIGS. 8, 9 and 10 show one section of the at least support member 6 based on a slotted tube design with lattice struts 31 arranged in a diamond-shaped manner, wherein annular surfaces 32 are formed as contact zones 15 at different points of this structure and are connected to the structure of the at least one support member 6 via meandering connecting webs 16.

As is clear from FIGS. 9 and 10, the meandering connecting webs 16 compensate for the expansion movement of the lattice struts 31 and ensure that the annular surfaces 32 remain far outwards in the radial direction and protrude radially beyond the contour of the at least one support member 6.

Figure 11:
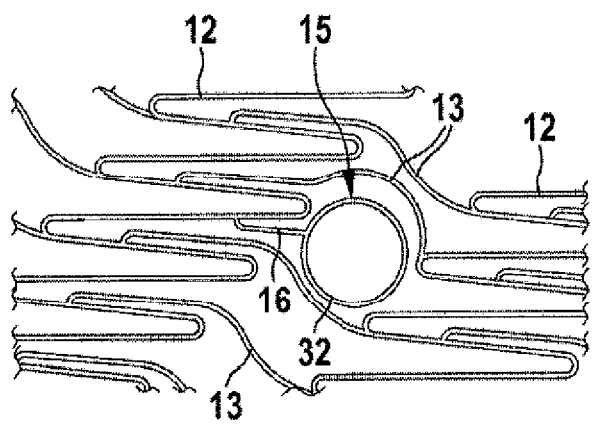
FIGS. 11-12 show another embodiment of a support member with meander struts.
Figure 12:
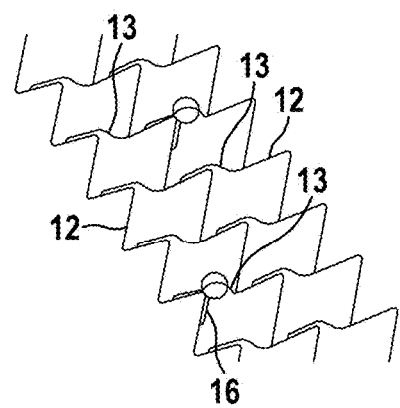

A further example of a section of a support member design with main meander struts 12, curved longitudinal bridge struts 13 and a contact zone 15, designed as an annular surface 32, of the electrode contact elements 14 is shown in FIGS. 11 and 12. The contact zones 15 are in this case connected to the main meander struts 12 via a single, narrow connecting web 16. As can be seen from FIG. 12, the annular surfaces 32, which, in the contracted position, are embedded into the structure between two curved bridge struts 13, slide outwardly beyond the bridge struts 13 during the expansion process, whereby the contact with the surrounding tissue is again ensured.

The basic designs of the at least one support member 6 shown in FIGS. 8-12 are known in principle as a "closed-cell" slotted tube design (closed cell design), apart from the additions provided in accordance with the present invention.

Figure 13:
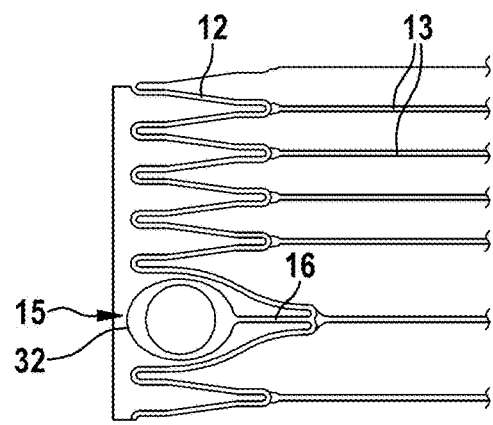
FIG. 13 shows another embodiment of a support member with a segment having main meander struts and longitudinally extending bridge struts.

An individual segment having main meander struts 12 and longitudinally extending bridge struts 13 is illustrated in FIG. 13, wherein a contact zone 15 formed as an annular surface 32 is again connected between two meander curves to the main meander struts 12 via a connecting web 16.

Additional apertures can—like the description before—be provided, which are used to incorporate radiopaque capabilities into the at least one support member 6. Additionally or alternatively, a selection of or all of the above illustrated apertures can be used for incorporation of radiopacity. Buttons made of dense materials suitable to be visible under X-ray conditions, can be inserted into these holders.

Alternatively or additionally, parts of the at least one support member 6 like struts or the holders are made of a biodegradable, biodissolvable, bioresorbable, biocorrodible or bioabsorbable radiopaque material.

Figure 14:
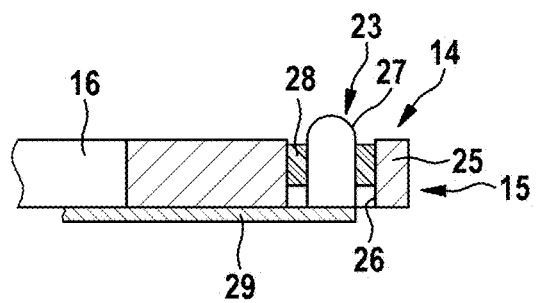
FIG. 14 shows an embodiment of a support member with a printed circuit board.

In the embodiment illustrated in FIG. 14, the electrode head 27 likewise sits in a galvanically decoupled manner, via the ring insulator 27, in the aperture 26 of the mechanical holder 25, which is formed by the contact zone 15, but a printed circuit or printed circuit board 29 is in this case provided beneath the contact zone 15. The electrode head 27 is being assembled on said printed circuit 29 and is being connected accordingly to the medical implant via strip conductors (not illustrated in greater detail). The printed circuit 29 may completely or in parts replace the filaments 3. The printed circuit is being composed of, for example, liquid crystal polymer with embedded conductive filaments. The circuit is adapted so as to conform to the at least one support member and allow encapsulation of itself into the vessel wall as the at least one support member dissolves. Additionally, electrical components may be embedded into the non-absorbable circuit to provide additional functionality such as, for example, multiplexing, power generation, stimulus generation, or sensory functions. The functionality of multiplexing has been previously described. The printed circuit or printed circuit board 29 may also be looped through one of the recesses named above, so that it extends on the outer surface of the at least one support member.

Figure 15:
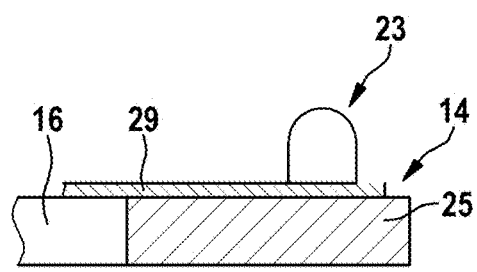
FIG. 15 shows another embodiment of a support member with a printed circuit board.

In the embodiment illustrated in FIG. 15, the electrode head 27 is likewise assembled on a printed circuit board 29, wherein this sits on the mechanical holder 25 however, such that the aperture 26 can be omitted. The electrode head 27 is again supplied with therapeutic stimuli via strip conductors on the printed circuit board 29.

Materials

1. Support Member.

Preferred materials for the support member 6 are magnesium alloys comprising a magnesium alloy of the following composition:

Magnesium: >90%
Yttrium: 3.7%-5.5%
Rare earths: 1.5%-4.4% and
Balance: <1%

This alloy is also known under the name WE43 and is subject matter of Assignee's U.S. Publication No. 2004/0098108, which disclosure is incorporated herein by reference in the present patent application in its entirety.

Further preferred are mechanically and/or electromechanically improved magnesium alloys, for example, the one of the following examples.

Example 1 for suitable biodegradable materials comprises a magnesium alloy, which comprises: no more than 3% by weight of Zn, no more than 0.6% by weight of Ca, with the rest being formed by magnesium containing impurities, which favor electrochemical potential differences and/or promote the formation of intermetallic phases, in a total amount of no more than 0.005% by weight of Fe, Si, Mn, Co, Ni, Cu, Al, Zr and P, wherein the alloy contains elements selected from the group of rare earths with the atomic number 21, 39, 57-71 and 89-103 in a total amount of no more than 0.002% by weight. This alloy is subject matter of Assignee's International Publication No. WO 2014/001241, which disclosure is incorporated herein by reference in the present patent application in its entirety.

Example 2 names a magnesium alloy, which comprises: 3 to 7% by weight Zn, 0.001 to 0.5% by weight Ca, the remainder being magnesium containing total impurities, which promote electrochemical potential differences and/or the formation of intermetallic phases, in a total amount of no more than 0.0048% by weight wherein the total impurity contains:

individual impurities selected from the group of Fe, Si, Mn, Co, Ni, Cu, Al, Zr and P in an amount of not more than 0.0038% of weight; and alloying elements selected from the group of the rare earths having the ordinal numbers 21, 39, 57-71 and 89-103 in an amount of no more than 0.001% by weight.

This alloy is subject matter of Assignee's International Publication No. WO 2014/001241, which is incorporated herein by reference in the present patent application in its entirety.

Example 3 comprises a magnesium alloy having improved mechanical and electrochemical properties, comprising: less or equal 4.0% by weight Zn, 2.0 to 10.0% by weight Al, the alloy content of Al in % by weight being greater than or equal to the alloy content of Zn in % by weight, the remainder being magnesium containing impurities, which promote electrochemical potential differences and/or the formation of precipitations and/or intermetallic phases, in a total amount of no more than 0.0063% by weight of Fe, Si, Mn, Co, Ni, Cu, Zr, Y, Sc or rare earths having the ordinal numbers 21, 57-71 and 89-103, Be, Cd, In, Sn and/or Pb as well as P, wherein the matrix of the alloy is solid solution hardening due to Al and Zn and is also particle hardening due to the intermetallic phases formed of Mg and Al.

This alloy is subject matter of Assignee's International Publication No. WO 2014/001240, which is incorporated herein by reference in the present patent application in its entirety.

2. Galvanically Insulating Materials and Coating on the Inside and/or Outside of the Support Member Surface.

All insulating materials, which are used to galvanically decouple the electrically active area of the filaments 3 and/or contact zone 15 from the at least one support member 6, are degradable corrodible, absorbable, dissolvable or resorbable. Suitable materials are, for example, biodegradable polymers and can be one or more selected from:

Polydioxanone,
Polyglycolide,
Polycaprolactone,
Polylactide, comprising poly-L-lactide, poly-D,L-lactide, and copolymers as well as blends like poly(L-lactide-co-glycolide), poly(D,L-lactide-co-glycolide), poly(L-lactide-co-D,L-lactide), poly(l-lactide-co-trimethylene carbonate),
Triblockcopolymers,
Polysaccharides, comprising chitosan, levan, hyaluronic acid, heparine, dextrane, cellulose, polyhydroxyvalerate,
Ethylvinylacetate,
Polyethylenoxide,
Polyphosphorylcholine,
Fibrine, and
Albumine,

3. Therapeutical Active Substances.

The galvanically insulating material, as well as coatings on the at least one support member 6, can be loaded with therapeutical active substances like corticosteroids, Cox-2 inhibitors, platelet activating factor (PAF) inhibitors, thrombolytics, and anticoagulants. There are selected one or more of the following:

Non-genetic therapeutic agents include anti-thrombogenic agents such as heparin, heparin derivatives, urokinase, and PPack (dextrophenylalanine proline arginine chloromethylketone); antiproliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including—benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including [alpha]-antagonists such as prazosin and bunazosine, [beta]-antagonists such as propranolol and [alpha]/[beta]-antagonists such as labctalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and [beta]-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethaci[pi] and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-I and ICAM-I interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-[beta] pathway agents such as polyanionic agents (heparin, fucoidin), decorin, and TGF-[beta] antibodies, EGF pathway agents such as EGF antibodies, receptor antagonists and chimeric fusion proteins, TNF-[alpha] pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline. Numerous additional therapeutic agents useful for the practice of the present invention are also disclosed in U.S. Pat. No. 5,733,925 assigned to NeoRx Corporation, the entire disclosure of which is incorporated herein by reference in its entirety.

4. Filaments.

Filaments may be made of, for example, stainless steel, like MP36N, or titanium base alloys or platinum based alloys like PtIr alloys. The filaments may be coated with a thin non-corrodible, non-absorbable, non-dissolvable or non-resorbable coating selected from the group of parylene and polyurethane. Additionally or alternatively, the filaments can be coated with one of the degradable, corrodible, absorbable, dissolvable or resorbable polymers as mentioned above.

5. Marker Material.

Examples of these materials are radiopaque alloys, which are biodegradable, biodissolvable, bioresorbable, biocorrodible or bioabsorbable. Preferred are materials like these disclosed in the U.S. Publication Nos. 2007/0191708, 2008/0033530, 2008/0033533, 2008/0033576 and/or 2012/0116499, the entire disclosures of which are incorporated herein by reference in their entireties.

6. PCB (Printed Circuit or Printed Circuit Board).

All PCBs are made of biocompatible, non-corrodible, non-absorbable, non-dissolvable or non-resorbable materials like, for example, Liquid Crystal Polymer (LCP) or other similar materials.

Technical advantages of the present invention include, but are not limited to:

1) Its ease of implant—cardiologists familiar with vascular intervention devices will be comfortable with handling the device and its procedure.

2) Explantability—cardiologists are concerned with lead longevity, and patient care flexibility such that any therapy that a patient receives should be long lasting and also explantable in the case of failure or future therapy changes which make it unnecessary.

3) Flexibility—the disclosed invention allows selection from a plurality of electro-active filaments in order to optimize the location of stimulation delivery or recording. This allows gross positioning during implant and optimization post operation.

4) Lack of therapeutic side effects—the present invention allows access to the vagus nerve for stimulation in a way that does not require a potentially dangerous cuff around the nerve. In addition, access to the vagus nerve is below the recurrent laryngeal branch, such that stimulation side effects which are cause by conduction via this branch such as hoarseness or coughing reflex commonly seen with a cuff electrode will be absent.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An intravascular electrode lead for an intravascular stimulation device, the intravascular electrode lead comprising:
   an electrode shaft;
   at least one filament being made of a conductive, non-biodegradable material, running in a longitudinal direction within the electrode shaft and protruding distally beyond a distal end of the electrode shaft, each filament comprising at least one electrically active area; and
   at least one support member being arranged distally from the distal end of the electrode shaft and being dilatable from a compressed state to a radially expanded state, wherein the support member is attached to the at least one filament and made of a biodegradable material,
   wherein each of the at least one filaments define the at least one electrically active area, and
   wherein each of the at least one electrically active areas serve as a sensorial interface to record physiological signals and/or as a therapeutic interface to stimulate surrounding tissue.

2. The intravascular electrode lead of claim 1, wherein the at least one support member is made of a biodegradable metal or metal alloy.

3. The intravascular electrode lead of claim 2, wherein the at least one support member is made of a biodegradable metal alloy, and wherein the biodegradable metal alloy includes magnesium, iron or zinc as a main alloy component.

4. The intravascular electrode lead of claim 1, wherein the at least one support member includes a radially expandable framework of struts.

5. The intravascular electrode lead of claim 1, wherein the at least one support member includes electrode contact elements, which either build the electrically active area of the at least one filament or which are fixedly and electrically attached to the electrically active area of the at least one filament.

6. The intravascular electrode lead of claim 5, wherein the electrode contact elements include an electrode contact zone, which is displaced radially outwardly in the expanded state of the at least one support member.

7. The intravascular electrode lead of claim 5, wherein each of the electrode contact elements include an electrode head electrically connected with one of the at least one filament and providing a therapeutic contact surface.

8. The intravascular electrode lead of claim 1, wherein the electrode contact elements are distributed circumferentially and longitudinally over the at least one support member.

9. The intravascular electrode lead of claim 1, wherein the intravascular electrode lead is adapted to allow retraction of the at least one filament into the electrode shaft.

10. The intravascular electrode lead of claim 1, wherein the at least one filament is connected to an electrically conducting tether running within the electrode shaft.

11. The intravascular electrode lead of claim 10, wherein the tether comprises connecting leads for each of the at least one filament.

12. The intravascular electrode lead of claim 10, wherein at least one of the at least one support members, the tether or the at least one filament includes radiopaque markers.

13. The intravascular electrode lead of claim 10, wherein at least one of the at least one support members, the tether or the at least one filament includes drug eluting components.

14. The intravascular electrode lead of claim 1, wherein the at least one filament comprises at least one tissue fixture.

15. An intravascular stimulation device comprising:
   a pulse generator; and
   an intravascular electrode lead as defined in claim 1.

16. The intravascular electrode lead of claim 1, wherein the electrically active areas are at a distal portion of each filament.

17. An intravascular electrode lead for an intravascular stimulation device, the intravascular electrode lead comprising:
- an electrode shaft;
- at least one filament being made of a conductive, non-biodegradable material, running in a longitudinal direction within the electrode shaft and protruding distally beyond a distal end of the electrode shaft, each filament comprising at least one electrically active area; and
- at least one support member being arranged distally from the distal end of the electrode shaft and being dilatable from a compressed state to a radially expanded state, wherein the support member is attached to the at least one filament and made of a biodegradable material, and
- wherein the at least one filament is replaced in total or in part by a printed circuit board and wherein an electrode head is being assembled on the printed circuit board,
- wherein each of the at least one filaments define the at least one electrically active area, and
- wherein each of the at least one electrically active areas serve as a sensorial interface to record physiological signals and/or as a therapeutic interface to stimulate surrounding tissue.

18. The intravascular electrode lead of claim 17, wherein the electrically active areas are at a distal portion of each filament.

* * * * *